US006565502B1

(12) United States Patent
Bede et al.

(10) Patent No.: US 6,565,502 B1
(45) Date of Patent: May 20, 2003

(54) NEEDLE HOLDER ASSEMBLY

(75) Inventors: Jessica Bede, New York, NY (US); Mary Anne Dell, Pittsburgh, PA (US); Charles Thiele, Butler, PA (US)

(73) Assignee: Capintec, Inc., Ramsey, NJ (US)

( * ) Notice: Subject to any disclaimer, the term of this patent is extended or adjusted under 35 U.S.C. 154(b) by 0 days.

(21) Appl. No.: 10/090,448

(22) Filed: Mar. 4, 2002

(51) Int. Cl.[7] .............................. A61N 5/00; G21F 5/00
(52) U.S. Cl. ........................................ 600/7; 250/507.1
(58) Field of Search .................. 600/7–8; 604/115–117, 604/162, 164.04, 178, 192, 65; 250/507.1, 423 R, 506.1; 209/542, 544, 576

(56) References Cited

U.S. PATENT DOCUMENTS

| | | | | |
|---|---|---|---|---|
| 4,759,345 A | * | 7/1988 | Mistry | ........................... 600/8 |
| 6,113,529 A | | 9/2000 | Shi | |
| 6,248,968 B1 | * | 6/2001 | Suzuki et al. | ............... 209/576 |
| 6,323,501 B1 | * | 11/2001 | White et al. | ............. 250/507.1 |
| 6,428,504 B1 | * | 8/2002 | Riaziat et al. | ................. 604/65 |
| 6,508,786 B2 | * | 1/2003 | Huitema et al. | ............ 604/116 |

* cited by examiner

*Primary Examiner*—Eric F. Winakur
*Assistant Examiner*—Nikita R Veniaminov
(74) *Attorney, Agent, or Firm*—Martin Fleit; Paul D. Bianco; Fleit, Kain, Gibbons, Gutman & Bongini P.L.

(57) ABSTRACT

A needle holder for use in a seed handling assembly that is made as a box-like open-sided metal frame having a bottom, a top and opposed side frame members with a pair of steel shielding plates enclosing the sides of the frame. The top frame member defines at least one row of holes for receiving elongated needles containing radioactive seeds. Feet are attached to opposite sides of the frame to enable the needle holder to be free standing. Lifting elements are attached to the frame to enable the needle holder to be picked up and moved while needles are held in the needle holder and for a person lifting and moving the needle holder to be shielded from radioactive seeds in a needle.

7 Claims, 3 Drawing Sheets

NEEDLE HOLDER ASSEMBLY

BACKGROUND OF THE INVENTION

1. Field of the Invention

The present invention relates to a needle holder assembly for a seed handling system that functions to assemble radioisotope seeds for medical applications.

2. Prior Art

In seed handling apparatus used for assembling radioisotope seeds for medical applications, a needle holder is used for holding a plurality of needles, for example 10 to 15 needles, each loaded with a plurality of radioisotope seeds and blank spacers in a predetermined pattern, aligned longitudinally or axially. According to the prior art, such a needle holder is shown and described in U.S. Pat. No. 6,113,529. Unfortunately, the needle holder depicted in the aforesaid patent has the disadvantage that in order to support the needle holder, it must either be inserted into a fitting on the rear of the seed handling apparatus of which it forms a part, or it must be laid flat. Whereas this is stated to be an advantage, according to the patent disclosure, because an X-ray can be taken of the needles, while they are lying flat, to insure that they are loaded properly, nevertheless, the proposal according to the patent suffers the disadvantage of the needle holder having to be supported whenever it is in the upright position. Further, the needle holder according to the patent is limited to holding a single row of needles, aligned in a common plane.

SUMMARY OF THE INVENTION

The principal object of the present invention is to provide a needle holder for a seed handling system that is more versatile. This is accomplished by providing a needle holder that is provided with special features to enable the needle holder to maintain itself in a stable vertical position, while at the same time, being enabled to be transported easily from one location to another. While in a vertical self-supporting position, the needle holder can be placed in proper juxtaposition to a seed handling apparatus, such as a table provided with a suitable shield for an operator. A sorting tray positioned on the shielded table allows the operator to select seeds or blanks and load the needles held vertically in the novel needle holder. A further novel feature of the present invention is the provision of a novel needle holder that has two staggered rows of openings to receive needles in two staggered rows thereby holding twice the number of needles possible with the needle holder of the prior art. Another advantage of the novel needle holder is that it is fully shielded at all times.

In a further refinement of the invention, it is an object to provide a needle holder for use in a seed handling assembly comprising a box-like open-sided metal frame having a bottom, a top and opposed side frame members, a pair of steel shielding plates enclosing the sides of the frame, the top frame member defining a at least one row of holes for receiving elongated needles containing radioactive seeds. Feet attached to opposite sides of the frame to enable the needle holder to be free standing, and lifting elements attached to the frame to enable the needle holder to be picked up and moved while needles are held in the needle holder and for a person lifting and moving the needle holder to be shielded from radioactive seeds in a needle.

The needle holder can have two rows of staggered holes defined in the top frame member. The needle holder can be arranged such that the feet are disposed normal to the planes of the steel shielding plates, and in a further refinement, each foot can comprise a trapezoidal plate with the small base attached to the side frame member and the large base serving as the bearing surface to maintain the needle holder free standing.

The lifting elements of the needle holder can be posts attached to the top portions of the side frame members and extend normal thereto terminating in free ends.

It is a further object of the invention to provide a needle holder for use in a seed handling assembly comprising a box-like open-sided metal frame having a bottom, a top and opposed side frame members, a pair of steel shielding plates enclosing the sides of the frame, the top frame member defining a at least one row of holes for receiving elongated needles containing radioactive seeds, feet attached to opposite sides of the frame to enable the needle holder to be free standing, each foot comprising a trapezoidal plate with the small base attached to the side frame member and the large base serving as the bearing surface to maintain the needle holder free standing, and posts attached to the top portions of the side frame members and extending normal thereto terminating in free ends to enable the needle holder to be picked up and moved while needles are held in the needle holder and for a person lifting and moving the needle holder to be shielded from radioactive seeds in a needle. Also, in this construction, the needle holder can have two rows of staggered holes defined in the top frame member.

Essentially, it is an object of the invention to provide a needle holder for use in a seed handling assembly that is made as a box-like open-sided metal frame having a bottom, a top and opposed side frame members with a pair of steel shielding plates enclosing the sides of the frame. The top frame member defines at least one row of holes for receiving elongated needles containing radioactive seeds. Feet are attached to opposite sides of the frame to enable the needle holder to be free standing. Lifting elements are attached to the frame to enable the needle holder to be picked up and moved while needles are held in the needle holder and for a person lifting and moving the needle holder to be shielded from radioactive seeds in a needle.

Other and further objects and advantages of the present invention will become more readily apparent from the following detailed description of preferred embodiments of the invention described in detail hereinafter.

DETAILED DESCRIPTION OF PREFERRED EMBODIMENTS

Figure 1:
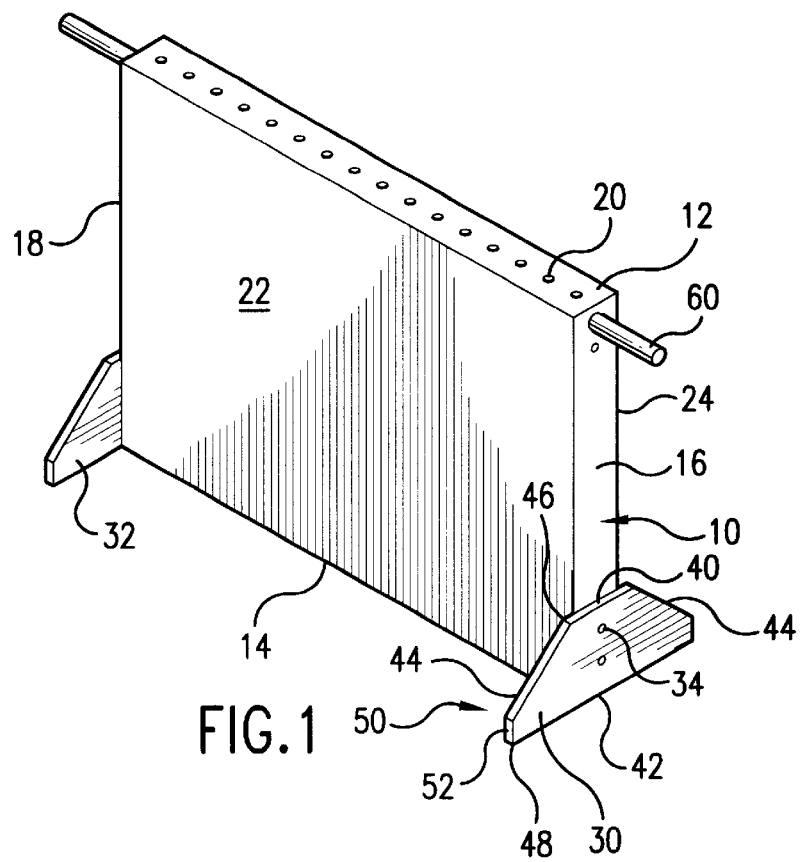
FIG. 1 is perspective view of a needle holder of the present invention showing a first preferred embodiment having a row of aligned holes for receiving needles.

Referring to the drawings, two preferred embodiments will now be described in detail. The first embodiment is shown in FIG. 1 and consists of a metal frame 10, preferably stainless steel, having an elongated top plate 12, an elongated bottom plate 14 and two side plates 16 and 18, which are joined together by any known and suitable arrangement to form an open rectangular box. The top plate 12 is drilled with a single row of spaced holes 20 to enable an elongated glass needle, closed at its free end and open at its top, to receive seeds or blanks serially inserted into the glass tube of the needle where they will be held in axial alignment. Such needles are well known in the art and the manner of use is well known in the art and no effort will be made to describe them in more detail. The front and rear sides of the needle holder consist of rectangular stainless steel plates 22 and 24 that close off the rectangular box of the frame parts to provide the requisite radioactive shielding for the needles that when loaded contain radioisotopes in the form of seeds.

At each side of the needle holder, at the bottom, are attached trapezoidal plates 30 and 32. The plates 30, 32 are attached by screws 34, as shown, but may be attached by other fastenings as will be well known to those of skill in the art. The plates 30, 32 have a short minor base 40 that is equal in width to the frame side part 16, and a substantially larger major base 42, about 2.5 to 4 times larger than the minor base 40. The side edges 44 of the plates 30, 32 extend at generally 45 degrees to the vertical from the opposed ends 46 of the minor base toward the opposed ends 48 of the major base. The lower edges of side edges 44 are cutoff at 50 to form vertical short edges 52 that interconnect the lower ends of the side edges 44 with the ends of the major base 42. The effect is as if the plates 30, 32 were isosceles triangles with the apexes of their angles cutoff, the minor base 40 being the top cutoff, and the short vertical edges 52 being the side cutoffs. The plates 30, 32 extend at right angles to the main plane of the needle holder, i.e., the steel side plates 22, 24.

At the top of the needle holder, on either side, is a projecting short cylindrical stub or post 60 that extends normally to either side of the needle holder. The posts 60 are each circular in cross section and are attached at one end to the top of the frame side parts 16 and 18, respectively. The free ends of the posts 60 extend outwardly parallel to the top frame part 12 and as an extension thereof, and serve as carrying handles to transport the needle holder from it place of loading to its place of utilization. In this process, the posts are suitably shielded by the two steel side plates 22, 24.

Figure 2:
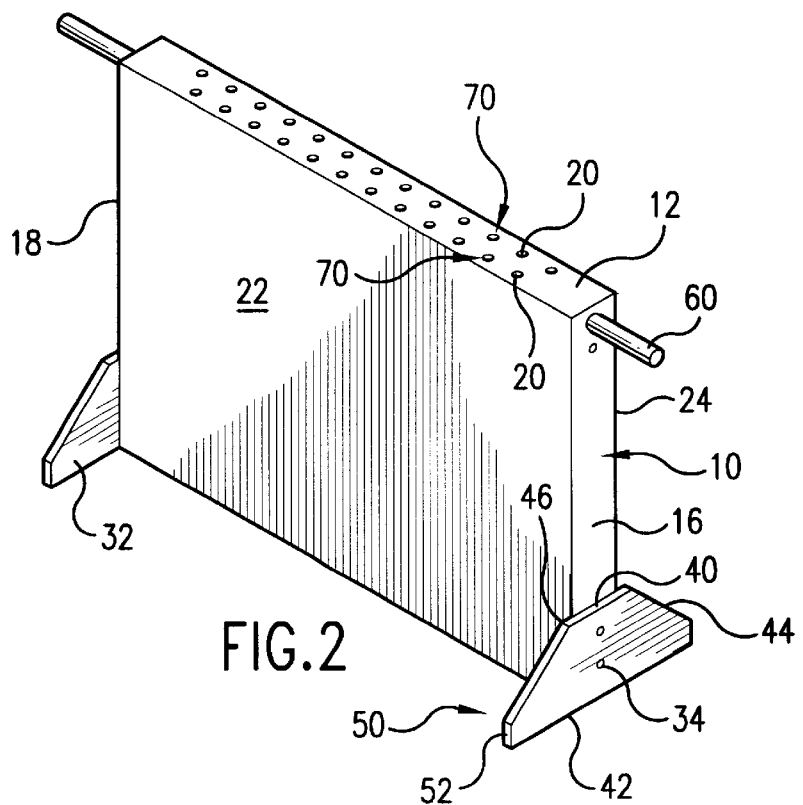
FIG. 2 is a perspective view of a needle holder of the present invention showing a second preferred embodiment having two staggered rows of holes.

The second embodiment is the same in construction as the embodiment of FIG. 1 and all like parts have been given the same reference numbers. The only difference resides in the fact that the embodiment of FIG. 2 has two staggered rows 70 of holes 20 for holding needles, that is, the holes 20 of one row are staggered with respect to the holes 20 in the other row. In this regard, the frame may be made wider to accommodate the two rows of holes.

Figure 3:
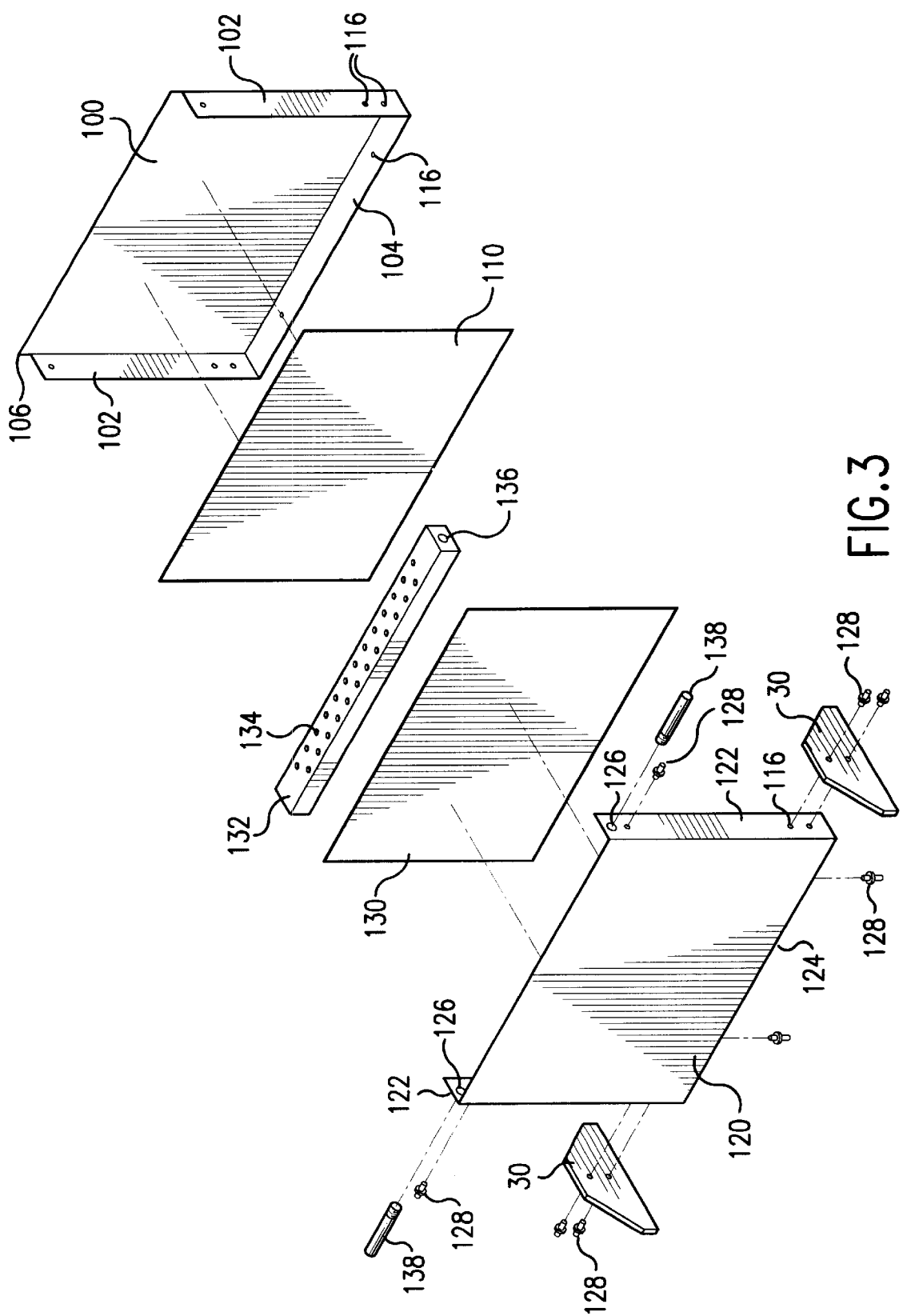
FIG. 3 is an exploded view of the needle holder shown in FIG. 2.
Figure 4:
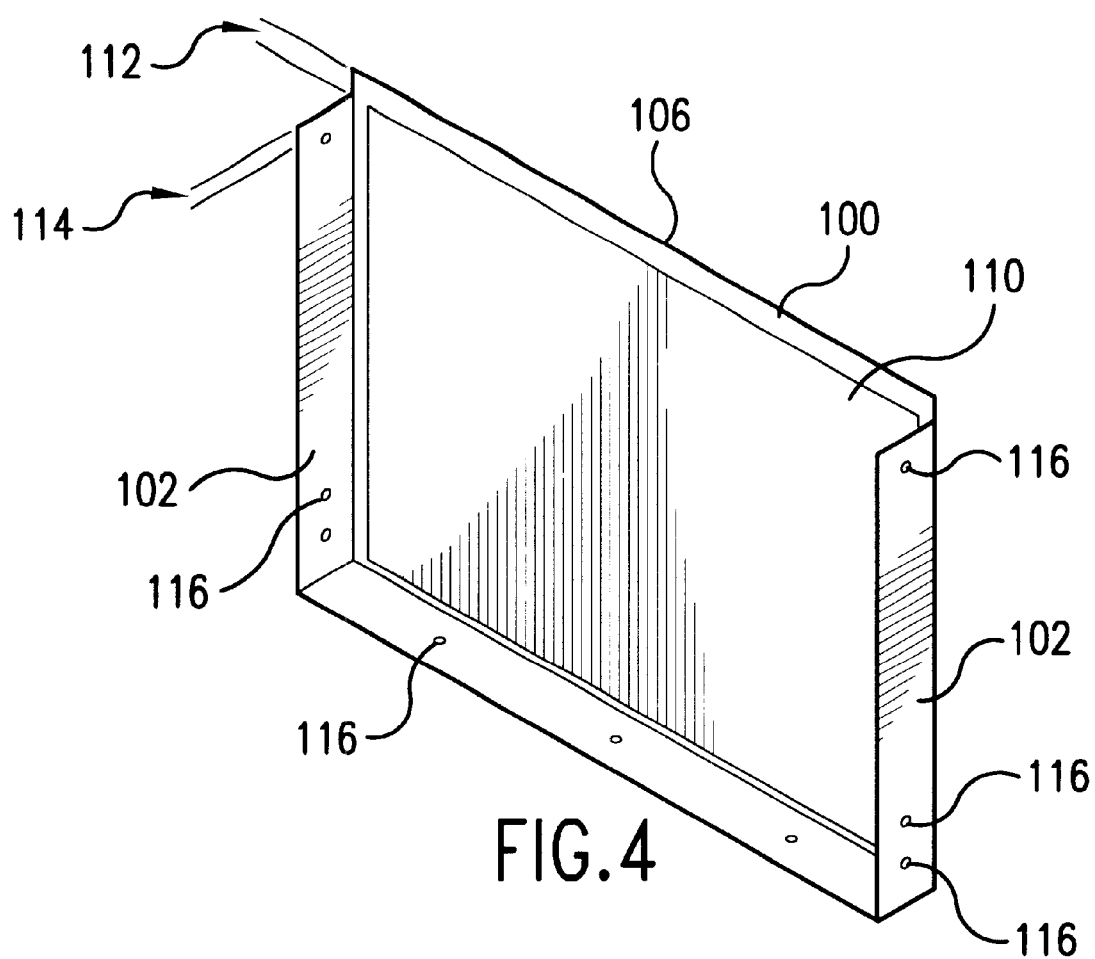
FIG. 4 is a perspective view of the back plate showing the mounting of the bearing plate.

In FIGS. 3 and 4 there is shown in greater detail the component parts of the needle holder and the arrangement considered as the best mode. As shown, the needle holder consists of a rear plate 100 bent to form side portions 102 and a bottom portion 104. The upper edge of the plate 100 extends above the tops of the side portions 102 as indicated by the reference number 106. A bearing plate 110 is glued by welding to the inside of the plate 100 in the manner shown in FIG. 4 to leave the clearances indicated by reference numbers 112 and 114, respectively, from the upper edges of the side portions 102 and the upper edge of the plate 100. The plate 100 is provided with holes 116 in the side portions and the bottom portions 104, which enable rivets to be inserted, as will become evident hereinafter.

The needle holder also has a front plate 120 that has bent in side portions 122 and bottom portion 124, all of which are provided with corresponding holes 116 to register with the holes 116 formed in the back plate 100. In addition, the front plate 120 has a pair of larger holes 126 formed at the top of the side bent-in portions 122. The front plate is provided with a bearing plate 130 that is glued by welding to the inside of the front plate in the manner shown for the rear plate 100. The rivets to fasten the plates 100 and 120 together are indicated as reference number 128. It will be noted that the feet 30, made of stainless steel, are fastened to the frame construction via the bottom rivets 128, as shown at the lower left corner of the drawing. The plates 100 and 120, as well as the bearing plates 110 and 120, are made of stainless steel and the rivets 128 are steel.

A stainless steel bar 132, provided or formed with countersunk through holes 134, in two rows of staggered holes, has tapped holes 136 in opposite ends as shown in FIG. 3. The bar 132 is fitted into the top opening of the frame made by riveting the two plates 100 and 120 together, and rests on the bearing plates 110 and 130, and is securely held by threaded tapered stainless pins 138 that pass through the holes 126 at the top of the side portions 122 of the front plate 120 and are threaded into the tapped holes 136, as shown in the drawing.

Although the invention has been shown and described in terms of specific preferred embodiments, nevertheless changes and modifications are possible that will appear evident to those skilled in the art from the teachings of the invention. Such changes and modifications are deemed to fall within the purview of the claimed invention.

What is claimed is:

1. A needle holder for use in a seed handling assembly comprising a box-like open-sided metal frame having a bottom, a top and opposed side frame members, a pair of steel shielding plates enclosing the sides of the frame, the top frame member defining at least one row of holes for receiving elongated needles containing radioactive seeds, feet attached to opposite sides of the frame to enable the needle holder to be free standing, and lifting elements attached to the frame to enable the needle holder to be picked up and moved while needles are held in the needle holder and for a person lifting and moving the needle holder to be shielded from radioactive seeds in a needle.

2. A needle holder according to claim 1 wherein two rows of staggered holes are defined in the top frame member.

3. A needle holder according to claim 1 wherein the feet are disposed normal to the planes of the steel shielding plates.

4. A needle holder according to claim 1 wherein each foot comprises a trapezoidal plate with the small base attached to the side frame member and the large base serving as the bearing surface to maintain the needle holder free standing.

5. A needle holder according to claim 1 wherein the lifting elements are posts attached to the top portions of the side frame members and extend normal thereto terminating in free ends.

6. A needle holder for use in a seed handling assembly comprising a box-like open-sided metal frame having a bottom, a top and opposed side frame members, a pair of steel shielding plates enclosing the sides of the frame, the top frame member defining at least one row of holes for receiving elongated needles containing radioactive seeds, feet attached to opposite sides of the frame to enable the needle holder to be free standing, each foot comprising a trapezoidal plate with the small base attached to the side frame member and the large base serving as the bearing surface to maintain the needle holder free standing, and posts attached to the top portions of the side frame members and extending normal thereto terminating in free ends to enable the needle holder to be picked up and moved while needles are held in the needle holder and for a person lifting and moving the needle holder to be shielded from radioactive seeds in a needle.

7. A needle holder according to claim 6 wherein two rows of staggered holes are defined in the top frame member.

* * * * *